United States Patent [19]

Smith

[11] Patent Number: 5,039,487
[45] Date of Patent: Aug. 13, 1991

[54] METHODS FOR QUANTIFYING COMPONENTS IN LIQUID SAMPLES

[75] Inventor: Kendall O. Smith, Boerne, Tex.

[73] Assignee: Board of Regents, The University of Texas System, Tex.

[21] Appl. No.: 518,123

[22] Filed: May 3, 1990

Related U.S. Application Data

[62] Division of Ser. No. 137,410, Dec. 22, 1987, Pat. No. 4,950,455.

[51] Int. Cl.$^5$ .................. G01N 1/28; G01N 33/48
[52] U.S. Cl. .................................. 422/56; 422/99; 422/73; 436/527; 436/520; 436/810
[58] Field of Search .................................. 422/57-58, 422/73, 99, 101, 56; 435/805; 436/10, 63, 520, 527, 810

[56] References Cited

U.S. PATENT DOCUMENTS

| | | |
|---|---|---|
| 1,724,953 | 8/1920 | Meyer . |
| 2,519,997 | 8/1950 | Brown . |
| 2,610,541 | 9/1952 | Rowland, Jr. . |
| 3,084,591 | 4/1963 | Stevens . |
| 3,198,064 | 8/1965 | Moore . |
| 3,275,834 | 9/1966 | Stevens . |
| 3,447,863 | 6/1969 | Patterson . |
| 3,503,684 | 3/1970 | Preston, Jr. et al. . |
| 3,558,522 | 1/1972 | Louderback . |
| 3,574,137 | 4/1971 | Decasperis . |
| 3,632,735 | 1/1972 | Kita . |
| 3,640,896 | 2/1972 | Decasperis . |
| 3,883,247 | 5/1975 | Adams . |
| 3,884,579 | 5/1975 | Mauthner . |
| 3,992,158 | 11/1976 | Przybylowicz . |
| 4,022,521 | 5/1977 | Hall et al. . |
| 4,076,419 | 2/1978 | Kleker . |
| 4,099,886 | 7/1978 | Oliveira . |
| 4,171,866 | 10/1979 | Tolles . |
| 4,193,980 | 3/1980 | Clason et al. . |
| 4,258,001 | 3/1981 | Pierce et al. . |
| 4,287,087 | 9/1981 | Brinkhous et al. . |
| 4,346,018 | 8/1982 | Carter et al. . |
| 4,444,880 | 4/1984 | Tom . |
| 4,501,496 | 2/1985 | Griffin . |

FOREIGN PATENT DOCUMENTS

0259137 3/1988 European Pat. Off. .

Primary Examiner—Robert J. Warden
Assistant Examiner—Lyle Alexander
Attorney, Agent, or Firm—Arnold, White & Durkee

[57] ABSTRACT

System for quantifying components in a liquid sample, for example white blood cells in blood, based on use of substantially non-compressible beads of uniform diameter as spacers between a microscope slide and a cover slip. The distance between the slide and cover slip is determined by the diameter of the beads, and thus the volume of the sample being viewed can be precisely determined. Prior to use, the beads may be adhered to a microscope slide or stirring rod in a dried adhesive matrix which is soluble in the liquid sample to be examined.

20 Claims, 3 Drawing Sheets

METHODS FOR QUANTIFYING COMPONENTS IN LIQUID SAMPLES

This is a divisional of copending application Ser. No. 137,410, filed Dec. 22, 1987 now U.S. Pat. No. 4,950,455.

BACKGROUND OF THE INVENTION

1. Field of the Invention

This invention relates to methods and apparatus for quantifying components in liquid samples. The methods and apparatus of the present invention may be broadly applied for use in quantifying components in various liquid samples, and may be more specifically applied for use in the counting of white blood cells.

2. Description of the Prior Art

Quantification of components in liquid samples is a necessary procedure in many scientific fields. In medical diagnoses, quantification of components in various body fluids is often a useful tool. For example, the counting of white blood cells or red blood cells in a patient's blood can indicate various diseases or infections which the patient may have contracted. Quantification is also involved in the counting of spermatazoa in semen.

Various methods and equipment are known in the art for quantifying components in liquid samples. State of the art electronic equipment, such as the "Coulter Counter" (registered trademark of Coulter Electronics, Inc.), can be used for this purpose. However, such equipment can be very expensive, costing on the order of several thousands of dollars, upwards to tens of thousands of dollars. Thus, this option is often not available to hospitals and laboratories having low budgets, as is often the case in poorer or less developed countries than the . United States.

Another method of quantifying components in liquid samples involves physically counting the components under a microscope in a known volume of the liquid sample. The volume is typically determined by multiplying the viewing area of the microscope by the thickness of the counting chamber. Various liquid sample holders have been designed for such purpose and are constructed so as to provide chambers of known and exact thickness. This has been achieved, for example, by precision grinding and cutting of glass, or the use of molded plastics, as disclosed in U.S. Pat. No. 4,501,496. Another counting chamber uses accurately drawn wire spacers which are permanently bonded between two sheets of glass, as disclosed in U.S. Pat. No. 3,198,064.

However, there are several disadvantages associated with the devices known in the prior art. First, the manufacturing cost involved is relatively high resulting in a high price to the consumer. Second, if it is necessary to mix the sample with a diluent before counting components in the sample, various other equipment must also be used. For example, before counting white blood cells in a blood sample, the red blood cells must typically be lysed by a hemolysing solution. (By "hemolysing solution" is meant a reagent that will selectively lyse red blood cells but not white blood cells). With the devices known in the prior art, the hemolysing solution and blood must first be pipetted to accurately determine the volume of each and then mixed in a dluting chamber so that the percent volume of diluent and blood in the mixture is known. Only after this procedure is complete can the sample be applied to the counting chamber in order to quantify the white blood cells.

In medical procedures, there is a need for great care in handling blood samples and other body fluids containing various infectious agents such as hepatitis and AIDS viruses. Therefore, it is desirable to use laboratory disposables as much as possible. In the quantification of components in liquid samples, the exposure risk of the worker to viruses within the samples is high during handling of the samples and quantification of components within the samples. Thus, it would be a particular advantage in the field of quantification of components in liquid samples if the counting chambers used were so inexpensive that they could be discarded after use However, because of the high costs in manufacturing the above-described counting chambers and their resulting high price, it is not economical to dispose of them after use.

Thus, it would be an advance in the art if a prevision made, disposable counting chamber were developed.

It is accordingly an object of this invention to provide methods and apparatus for quantifying components in liquid samples which can overcome or reduce the disadvantages of the prior systems.

SUMMARY OF THE INVENTION

In accordance with one aspect of the present invention, a microscope slide for use in quantifying components in a liquid sample is provided. A dried adhesive matrix which is preferably soluble in the liquid sample to be examined is affixed on the operative face of theslide. A plurality of substantially spherical beads uniform diameter made of a substantially non-compressible material are located within the adhesive matrix. A counting chamber is also provided by the present invention when a cover slip for positioning over the operative face of the slide is provided with the above-described microscope slide.

The adhesive matrix is preferably soluble in the liquid sample to be examined so that, as will be explained below in the discussion of the methods of quantification provided by the present invention, the liquid sample can be placed directly on the matrix. The sample and matrix may then be mixed to dissolve the matrix in the sample. However, the matrix could also be soluble in an intermediate diluent, so that the diluent could be placed directly on the matrix to dissolve it and then the liquid sample could be placed on the diluent. This is not preferred because the volume of diluent would need to be accounted for in the subsequent quantification.

The adhesive matrix may consist of a solid residue of dried adhesive liquid serving as a gluing agent-matrix for holding the beads over the operative face of the microscope slide until a liquid sample is mixed with the beads for quantification of components. The composition of the adhesive matrix will depend upon the application for which the microscope slide and counting chamber will be but to use. Preferably, the adhesive liquid used in forming the adhesive matrix is selected so that the adhesive matrix will be soluble in the liquid sample to be examined. For example, if the liquid sample to be examined is aqueous (e.g. semen), a suitable adhesive liquid is a dilute (e.g. 1%) solution of sucrose or other monosaccharide in water. A water soluble gelatin is also suitable. If the counting chamber is to be used for white blood cell counting, the adhesive liquid can consist of a hemblysing solution which will selectively lyse the red blood cells within a blood sample.

Use of a hemolysing solution as the adhesive liquid is particularly advantageous in this context, since the dried matrix of hemolysing solution will dissolve in a blood sample and lyse the red blood cells. It has been found that the optimum amount of lysing agent to use for selective destruction of red blood cells is a total solid weight of 0.052 mg/ml of blood to be treated. The optimum may be varied within a range of ±25% to give adequate results. This solid may consist of a dried residue of a hemolysing solution having the following contents, as disclosed in U.S. Pat. No. 4,346,018 (hereinafter "Lyse S III", Lyse S being a registered trademark of Coulter Electronics, Inc): quaternary ammonium salts (35-50 g/l), isopropanol (11-14 g/l), potassium cyanide (0.20-1.0 g/l), and surfactant (7-10 g/l). This optimum is based upon use with whole blood containing 9-15 gm% hemoglobin.

The adhesive matrix can be stable to suspend the beads over the microscope slide for many months. For example, dried hemolysing solution has been found to be stable at an average temperature of 20° C. and 37° C. for over 12 months without any noticeable loss of ability to selectively lyse red blood cells.

In the quantification methods which will be discussed below, the cover slip and slide are spaced apart by the beads by a known distance determined by the vertical dimension of the beads. Thus, the beads must have substantially uniform vertical dimension for the counting chamber to have uniform thickness throughout. Applicant has selected beads of spherical shape and uniform diameter to provide this function, although cubical or elliptical beads might also be used as spacers. A spherical bead is preferred since it has the same vertical dimension regardless of how it is situated between the slide and cover slip, and spheres cannot easily stack when compressed.

Spherical beads suitable for use are commercially available, for example, from Duke Scientific Corporation of Palo Alto, California. Such beads having specified tolerances provide accurate spacing means in the present invention. Typically, commercially available beads can be obtained having a specified nominal diameter and a standard deviation. For example, glass beads with a nominal diameter of 50 microns may have a 2.5 micron standard deviation. As should be appreciated, the distance between the microscope slide and cover slip of the counting chamber provided by the present invention is determined by the largest beads there between. Thus, for preferred accuracy in the quantification methods provided by the present invention, the diameter of the beads should be assumed to be the nominal diameter plus the standard deviation.

In a preferred embodiment, the beads are made of glass. Compressive forces are administered on the beads during quantification due in part to the weight of the cover slip, but more significantly due to the capillary action of the liquid sample between two slightly separated surfaces. These forces can be substantial; therefore, glass is preferred over plastic or other substances due to the near absolute rigidity of glass. Since the thickness of the counting chamber of the present invention is preferably assumed to be the diameter of the beads, lack of distortion of the spherical shape of the beads is important for accuracy. Furthermore, glass beads are preferable over plastic because they will visibly indicate over-compression by shattering, while plastic beads will tend to distort, not break.

When using the counting chamber for white blood cell counting, it is preferred that the diameter of each bead be between about 2-200 microns, with the optimum range being between about 40-60 microns.

Another embodiment of the invention provides for a mixture for use in connection with microscopic counting of while blood cells which includes a plurality of beads as described above dispersed within a hemolysing solution.

The present invention also provides a method for preparing the microscope slide with an adhesive matrix. This method includes the steps of mixing a plurality of the beads in an adhesive liquid. A quantity of this mixture is placed on the microscope slide and the adhesive liquid is allowed to dry to form the solid adhesive matrix on the microscope slide, the beads being located in the plug.

A method for quantifying components in a liquid sample is provided which uses the counting chamber described above. The method includes the steps of placing a liquid sample on the matrix of the microscope slide. The liquid sample and matrix are mixed with a stirring instrument so that the matrix dissolves in the liquid sample. A cover slip is placed over the sample and beads so that the cover slip rests on the beads and is spaced from the slide by a known distance determined by the diameter of the beads, thereby creating a counting chamber. The sample disposed between the slide and cover slip is viewed under magnification with a microscope. The components in a known volume of sample are then counted. The known volume is determined by measuring the viewing area of the microscope and multiplying the viewing area by the distance between the slide and cover slip as determined by the diameter of the beads. The viewing area of the microscope may be determined, for example, by using an ocular reticle of known line-spacing within the eye piece of the microscope.

The preferred number of beads on the slide during quantification is approximately 10 per square centimeter of counting chamber area, with a range of 5 to 30 beads per square centimeter giving adequate results. Greater numbers tend progressively to obstruct fields of view in the microscope where the specimen cells are to be counted, thus causing significant displacement of specimen components in the counting areas.

It is preferable for the volume of the liquid sample to be selected in relation to the size of the cover slip so that when the cover slip is placed over the liquid sample, the volume of the liquid sample and beads disposed between the slide and cover slip is less than the total volume available between the slide and cover slip; i.e., the volume of the liquid sample is not in excess. This assures that the cover slip will rest on top of the beads and not float above them, because the capillary force of the liquid acts to pull the cover slip towards the microscope slide. As will be appreciated, the exact thickness of the counting chamber is thus known, being determined by the diameter of the beads.

Approximating the ideal volume of the liquid is easy with experience, without use of a pipetting device; use of a pipet and a measured volume of the liquid sample is preferred if the technician is inexperienced. However, as long as the volume of the sample is not in excess, the quantification per unit volume is not affected by the size of the sample placed on the slide. For example, a series of white blood cell counts was performed on a single blood specimen using sample volumes of 2, 3, 4, 5 and 10 microliters. The counts per unit volume for the samples were substantially consistent.

The invention provides a method for counting white blood cells, when the matrix of the microscope slide consists of a solid residue of dried hemolysing solution. This method includes the steps of placing a sample of blood on the adhesive matrix and mixing the blood sample and matrix with a stirring instrument so that the matrix dissolves in the blood sample, and the red blood cells in the blood sample are lysed by the hemolysing constituents from the matrix. It should be appreciated that, because the hemolysing constituents are already present on the microscope slide in a dried state, the blood sample can be applied directly to the counting chamber without the need for pipetting or intermediate diluting. Because the dried hemolysing constituents are soluble in blood, the entire volume of liquid on the slide after dissolving the matrix can be assumed to be blood without significantly affecting the accuracy of the counting method. A cover s.lip is next placed over the blood sample and beads so that the cover slit rests on the beads and is spaced from the slide by a known distance determined by the diameter of the beads. The blood sample disposed between the slide and cover slip is when viewed under magnification with a microscope. The optimum magnification for counting white blood cells using this method has been found to be 200×, with a range of 100× to 400× yielding adequate results. The white blood cells in a known volume of the blood sample are counted. The known volume is again determined by measuring the viewing area of the microscope and multiplying the viewing area by the distance between the slide and cover slip as determined by the diameter of the beads.

Another embodiment of the present invention provides a standard microscope slide and counting chamber for testing the reliability of the above-described white blood cell counting method. The standard microscope slide consists of the above-described microscope slide with an adhesive matrix made of a solid residue of dried hemolysing solution. As described above, the adhesive matrix contains a plurality of substantially spherical beads of uniform diameter made of substantially noncompressible material. However, the matrix also contains a known number of control particles, fixed so as not to be destroyed by drying or lyse in the presence of the hemolysing solution, and shaped and sized so as to simulate human white blood cells. Suitable control particles include fowl or other red blood cells, preferably chicken red blood cells, which are formalin-fixed so as not to lyse in the presence of the hemolysing solution. Synthetic latex particles are also suitable. A standard counting chamber is provided by the present invention, when a cover slip is provided with the above-described standard microscope slide.

The invention also provides a mixture for use in connection with microscopic counting of white blood cells which includes beads and control particles as described above dispersed within a hemolysing solution, the concentration of control particles within the mixture being exact and known.

A method for preparing the standard microscope slide is provided which includes the steps of first mixing the beads in a hemolysing solution and then placing a quantity of the mixture on a microscope slide. A plurality of the control particles are separately mixed in distilled water so that the concentration of control particles in the water is exact and known. A known volume of the mixture of control particles in water is placed on the microscope slide with the mixture of beads and hemolysing solution. The water is then allowed to evaporate and the hemolysing solution is allowed to dry to form the adhesive matrix, the matrix being soluble in water. Thus, a known number of control particles are suspended in the matrix, the known number of control particles calculable from the known concentration and volume of water used.

Another method for preparing the standard microscope slide is provided including the steps of preparing a mixture of hemolysing solution, beads, and fixed control particles. The control particles are uniformly dispersed within the mixture, so that the concentration of fixed control particles within the mixture is exact and known. A known volume of this mixture is then placed on a microscope slide, and the hemolysing solution is allowed to dry to form the adhesive matrix, the matrix being soluble in water. A known number of control particles is thus suspended within the matrix, the number being calculable from the known concentration and volume of the mixture used.

The present invention also provides a method for testing the reliability of a white blood cell counting method using the standard microscope slide described above. This method includes the steps of placing a known volume $V_x$ of water on the matrix of the standard microscope slide. The water and matrix are mixed with a stirring instrument so that the matrix dissolves in the water. The actual concentration of control particles in the water is calculated based on the known number of particles in the matrix and the volume $V_x$ of water. A cover slip is placed over the water and beads so that the cover slip rests on the beads and is spaced from the slide by a known distance determined by the diameter of the beads. The control particles in the water disposed between the slide and cover slip are then viewed under magnification with a microscope. The control particles in a known volume $V_y$ of water are then counted. The volume $V_y$ is determined by measuring the viewing area of the microscope and multiplying the viewing area by the distance between the slide and cover slip as determined by the diameter of the beads. From the number of control particles counted within the known volume $V_y$ of water, a measured concentration of control particles in the water is obtained. This measured concentration of control particles is then compared to the actual concentration of control particles in the water. The lab technician is thus provided with a method of testing the accuracy and precision of his testing methods. Preferably, the volume $V_x$ of water is selected so that the actual concentration of control particles in the water after dissolving the matrix in water will be between about 5,000 to 10,000 particles per cubic millimeter, which number simulates the normal range of white blood cells within human blood.

The present invention also provides a microscope slide for use in quantifying components in a plurality of liquid samples. This microscope slide is similar to the previously described microscope slide except that a plurality of spaced adhesive matrices provided on the operative face of the microscope slide. Each adhesive matrix is soluble in the liquid sample having components to be quantified and each contains a plurality of substantially spherical beads of uniform diameter made of a substantially non-compressible material. One or more cover slips for positioning over the operative face of the slide may be provided to form a counting chamber. Thus, a single microscope slide can be used for examining several liquid samples.

It should be appreciated that a single matrix may be located proximate one end of a microscope slide, with the other end of the microscope slide unprepared for quantification. When this is done, quantification in accordance with the above-described methods may be performed on a portion of the slide while the remaining portion of the slide may be used for some other purpose, for example, a blood smear for later staining and examination. Thus, two tests may be done on one slide resulting in convenience and cost savings. For example, a lab technician could perform a white blood cell count in accordance with the present invention at one end of the microscope slide, and, if the count is unusual, do a quantitative differential white blood cell test at the other end.

A method of calibrating the viewing area of a microscope is also provided using the previously-described microscope slide having an adhesive matrix of dried hemolysing solution. This method includes the steps of mixing a plurality of control particles, fixed so as not to lyse in the presence of a hemolysing solution, in water, the concentration of the control particles in the water being exact and known. A quantity of this mixture is placed on the adhesive matrix of the microscope slide, and the water and matrix are mixed with a stirring instrument so that the matrix dissolves in the water. A cover slip is placed over the mixture and beads so that the cover slip rests on the beads and is spaced from the slide by a distance determined by the diameter of the beads. The control particles in the water disposed between the slide and cover slip are viewed under magnification with a microscope to be calibrated and the control particles in the viewing area of the microscope are counted. Preferably, the eye-piece of the microscope has a reticle or grid so that the control particles in each grid area can be counted. A calibration factor for the viewing area (or grid areas) of the microscope is determined by dividing the known concentration of control particles in water by the number of control particles counted in the viewing area of the microscope.

Preferably, the concentration of control particles in water is selected in relation to the viewing area of the microscope so that the number of control particles counted in the viewing area (or grid areas) will be about 400 or more. As should be appreciated, the precision of calibration increases with the increase in number of particles counted. Theoretically, the coefficient of variation (c.v.) varies with the following relationship:

$$c.v. = \frac{\sqrt{n}}{n} \times 100\%$$

where n is the number of particles counted. Thus, if 400 particles are counted, c.v. is 5.0%, which is adequate for most clinical laboratory TESTS.

An illustration of how this method of calibration would work is as follows. Assume an average of 100 control particles were counted per grid area and that the concentration of control particles in the water applied to the microscope slide was exactly 10,000 per mm³. Then the concentration of white blood cells (or other cells) in an unknown sample, similarly treated and counted by the disclosed method, would be:

$$\begin{aligned} \text{cells/mm}^3 &= (\text{Avg. count/grid area}) \times (\text{Calibration factor}) \\ &= (\text{Avg. count/grid area}) \times \frac{10,000}{100} \end{aligned}$$

For example, if an average of 50 cells per grid area were counted in the unknown sample, the calculation would be:

$$\text{cells/mm}^3 = 50 \times \frac{10,000}{100} = 5,000$$

A table of calculated values can therefore be constructed to cover a wide range of counts, put in tabular form, and no arithmetic calculations required thereafter in the work setting where counts are being done with the calibrated microscope.

In an alternative embodiment of the present invention, a stirring rod for use in quantifying components in a liquid sample is provided. The stirring rod has a dried adhesive matrix over at least one end portion, the adhesive matrix being soluble in a liquid sample having components to be quantified. In practice, the matrix adheres to the tip of the end portion of the stirring rod. Located within the adhesive matrix are substantially spherical beads of uniform diameter made of a substantially non-compressible material. The adhesive matrix is analogous to the adhesive matrix on the microscope slide described above. Thus, the adhesive matrix can be stable to suspend the beads over the end portion of the stirring rod for many months, and can be made of a solid residue of dried hemolysing solution when used in connection with white blood cell counting.

Preferably, the stirring rod has at least one bulbous end portion and the adhesive matrix is located over the bulbous end portion.

The present invention also provides a method for preparing the stirring rod described above including the steps of mixing a plurality of the beads in an adhesive liquid. A quantity of the mixture of beads and adhesive liquid is applied to an end portion of the stirring rod. The adhesive liquid is allowed to dry to form a solid, adhesive matrix at the end portion with a plurality of the beads located within the matrix, the matrix being soluble in a liquid sample to be examined. The adhesive liquid may be a hemolysing solution so that the rod may be useful in connection with white blood cell counting.

Preferably, the stirring rod is prepared by holding it in a vertical position and applying a quantity of the mixture of beads and adhesive liquid to the lower end portion of the stirring rod. In practice, the mixture flows down the rod to the tip of the lower end portion, and the adhesive liquid is allowed to dry to form the matrix over the tip of the lower end portion of the stirring rod.

A method for quantifying components in a liquid sample is also provided by the present invention using the stirring rod disclosed above. This method includes the steps of placing a liquid sample on a microscope slide and stirring the liquid sample with the stirring rod described above so that at least a portion of the adhesive matrix is dissolved in the liquid sample, thereby mixing a plurality of beads in the liquid sample. A cover slip is placed over the sample and beads so that the cover slip rests on the beads and is spaced from the slide by a known distance equal to the diameter of the beads. The sample disposed between the slide and cover slip is then viewed under magnification with a microscope. The components in a known volume of the sample are counted. The volume is determined by measuring the viewing area of the microscope and multiplying the viewing area by the distance between the slide and cover slip as determined by the diameter of the beads.

The present invention also provides a method for counting white blood cells when the adhesive matrix of the stirring rod described above is made of a solid residue of dried hemolysing solution. This method includes the steps of placing a sample of blood on a microscope slide and stirring the blood sample with the stirring rod until at least a portion of the matrix is dissolved in the blood sample, so that a plurality of beads are mixed in the blood, and the red blood cells in the blood sample are lysed by the hemolysing constituents from the matrix. A cover slip is placed over the blood sample and beads so that the cover slip rests on the beads and is spaced from the slide by a known distance equal to the diameter of the beads. The blood sample is disposed between the slide and cover slip is then viewed under magnification with the microscope. The white blood cells in a known volume of the blood sample are counted. The known volume is determined by measuring the viewing area of the microscope and multiplying the viewing area by the distance between the slide and cover slip as determined by the diameter of the beads.

BRIEF DESCRIPTION OF THE DRAWINGS

This invention is now described by reference appended drawings which illustrate particular preferred embodiments of the apparatus and methods provided by the present invention.

DETAILED DESCRIPTION OF PREFERRED EMBODIMENTS

For ease of illustration, some of the microscopic size elements included in the illustrated apparatus and methods have been enlarged out of scale.

Figures 1, 2:
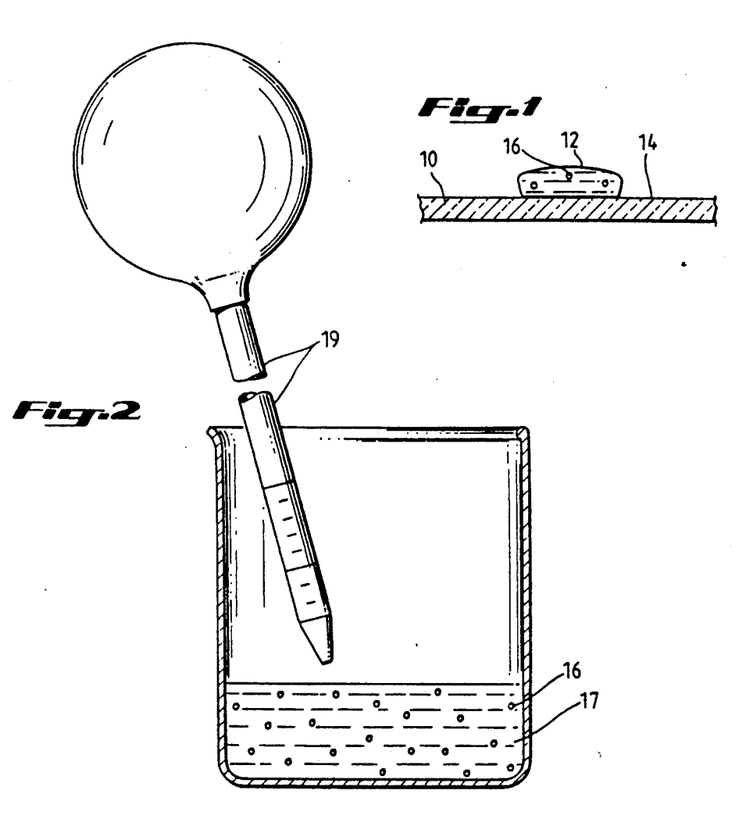
FIG. 1 is a fragmentary, sectional side view of a preferred embodiment of a microscope slide prepared according to the present invention.
FIG. 2 is a partially sectional side view illustrating another embodiment of the present invention.

Referring now to FIG. 1, a preferred embodiment of the present invention is shown. Microscope slide 10 is provided for use in quantifying components in a liquid sample having a dried adhesive matrix 12 located on the operative face 14 of the slide 10. A plurality of substantially spherical beads 16 are located within the adhesive matrix 12 (Beads 16 and matrix 12 are enlarged out of scale for ease of illustration). The beads 16 have uniform diameter at a value between 40 and 60 microns, and are made of a non-compressible material in the form of glass. The adhesive matrix 12 consists of a solid residue of dried liquid. If the microscope slide is to be used for quantification of components in an aqueous sample, the liquid consists of aqueous sucrose; if the slide is to be used for white blood cell counting, the liquid is a hemolysing solution. Adhesive matrix 12 is thus soluble in the liquid sample to be examined.

Figure 3A:
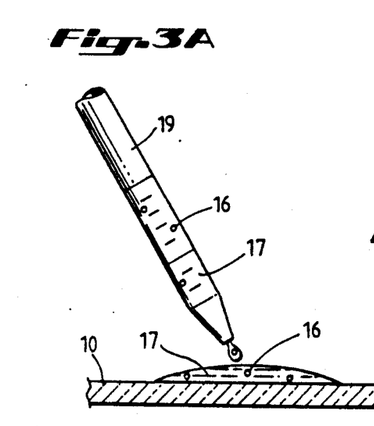
FIG. 3A is a fragmentary, partially sectional side view illustrating a method for preparing a preferred embodiment of a microscope slide in accordance with the present invention.

Referring now to FIGS. 2 and 3A, the microscope slide 10 is prepared by the method of mixing a plurality of the beads 16 in an adhesive liquid 17. A quantity of this mixture is applied to the microscope slide 10 by means of pipette 19. The adhesive liquid 17 is allowed to dry to form the adhesive matrix 12 on the slide 10.

Figure 4:
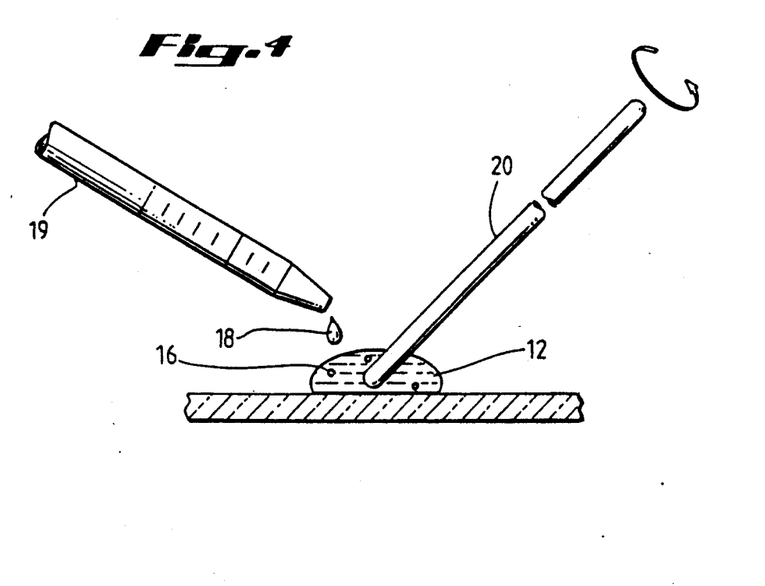
FIG. 4 is a fragmentary, partially sectional side view illustrating a preferred method for quantifying components in a liquid sample in accordance with the present invention.
Figure 5:
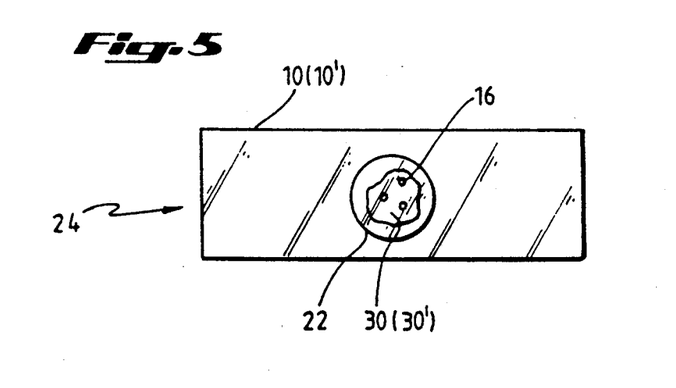
FIG. 5 is a plan view of a counting chamber provided by the present invention.
Figure 6:
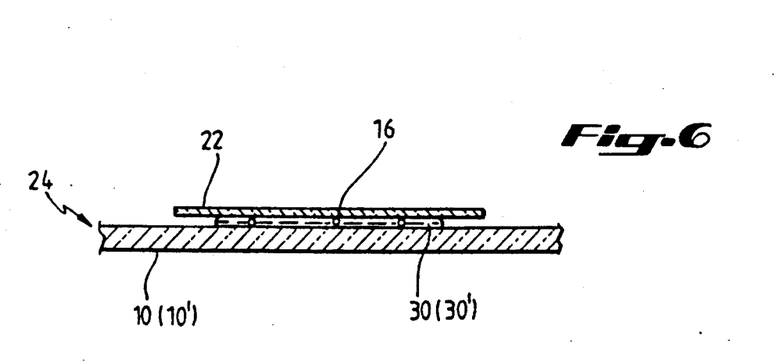
FIG. 6 is a fragmentary, sectional side view of a counting chamber provided by the present invention.

Referring now to FIGS. 4–6, a method for quantifying components in a liquid sample is provided which uses the microscope slide illustrated in FIG. 1. An aqueous liquid sample 18 is placed on the matrix 12 on the microscope slide 10 (Sample 18 and Matrix 12 are not drawn to Scale). The liquid sample 18 and matrix 12 are mixed with a stirring instrument 20 so that the matrix 12 dissolves in the liquid sample 18. The liquid sample with the matrix dissolved therein is denoted in the figures as 30. A cover slip 22 is placed over the sample 30 and beads 16 so that the cover slip 22 rests on the beads 16 and is spaced from the slide 10 by a known distance determined by the diameter of the beads 16, as shown in FIG. 6. The number of beads 16 on slide 10 is approximately 10 per square centimeter. Counting chamber 24 is then placed under a microscope so that the sample 30 disposed between the slide 10 and cover slip 22 is viewed under magnification. The components in a known volume of sample 30 are then counted. The known volume is determined by measuring the viewing area of the microscope and multiplying the viewing area by the distance between the slide 10 and cover slip 22 as determined by the diameter of the beads 16.

Preferably, the volume of liquid sample 30 is selected in relation to the size of cover slip 22 so that when cover slip 22 is placed over the liquid sample 30, the volume of the liquid sample 30 and beads 16 disposed between the slide 10 and cover slip 22 is less than the total volume available between the slide 10 and cover slip 22 as illustrated in FIGS. 3 and 4.

The apparatus and method illustrated in FIGS. 2–4 thus provide a quick and simple method for quantifying components in liquid samples, including white blood cells in blood. It is an advantage of this embodiment that it provides inexpensively manufactured apparatus having extremely precise spacing means to provide a counting chamber of known and exact thickness. The method overcomes disadvantages in the art by eliminating the need for intermediate diluting vessels or pipetting of samples and diluents.

FIGS. 1-6 equally illustrate a method and apparatus for counting white blood cells, when the matrix 12 consists of a solid residue of dried hemolysing solution 17. In this case, blood sample 18 is placed on adhesive matrix 12 and mixed with stirring instrument 20 so that matrix 12 dissolves in blood sample 18, and the red blood cells in the blood sample are lysed by the hemolysing constituents from matrix 12. Sample 30 thus comprises blood having red blood cells lysed, so that the white blood cells within the blood can be more conveniently counted in accordance with the steps provided above. An advantage of this aspect of the invention over prior-known systems is that the blood need not be diluted with hemolysing solution in an intermediate vessel before counting. By providing an adhesive matrix of dried hemolysing solution, the blood sample can be administered directly upon the slide.

FIG. 1 also illustrates a standard microscope slide prepared in accordance with the present invention for testing the reliability of the white blood cell counting method described above. In this case, the adhesive matrix 12 again comprises a solid residue of dried hemolysing solution. As described above, the adhesive matrix 12 contains a plurality of substantially spherical glass beads 16 of uniform diameter. The matrix further contains a known numb.er of chicken red blood cells, which are formalin-fixed so as not to be destroyed by drying or lyse in the presence of the hemolysing solution. The chicken red blood cells, of course, are not visible except under magnification.

Referring to FIGS. 2 and 3A, the standard microscope slide 10 is prepared by mixing the beads 16 in the hemolysing solution 17 and then placing a quantity of the mixture on the microscope slide I0. A plurality of the chicken red blood cells are separately mixed in distilled water so that the concentration of control particles in the water is exact and known. A known volume of the mixture of chicken red blood cells in water is placed on a microscope slide 10 with the mixtures of beads 16 and hemolysing solution. The water is then allowed to evaporate and the hemolysing solution is allowed to dry to form the adhesive matrix 12.

The standard microscope slide 10 can also be prepared by preparing a mixture of hemolysing solution 17, beads 16, and chicken red blood cells. The chicken red blood cells are uniformly dispersed within the mixture, so that the concentration of chicken red blood cells within the mixture is exact and known. A known volume of this mixture is then placed on the microscope slide 10 by means of pipette 19, and the hemolysing solution 17 is allowed to dry to form the adhesive matrix 12.

FIGS. 4-6 also illustrate a method for testing the reliability of a white blood cell counting method using the standard microscope slide illustrated by FIG. 1 and described above. This method includes the steps of placing a known volume $V_x$ of Water 18 on the matrix 12. The water 18 and matrix 12 are mixed with a stirring instrument 20 so that the matrix 12 dissolv(R)s in the water. The water with the matrix dissolved therein is denoted in the figures as 30. The actual concentration of chicken red blood cells in the water 30 is calculated based on the known number of particles in the matrix 12 and the volume $V_x$ of water 18. Cover slip 22 is placed over the water 30 and beads 16 so that the cover slip 22 rests on the beads 16 and is spaced from the slide 10 by a known distance determined by the diameter of the beads 16 The chicken red blood cells in the water 30 disposed between the slide 10 and cover slip 22 are then viewed under magnification with a microscope. The chicken red blood cells in a known volume $V_y$ of water 30 are then counted. The volume $V_y$ is determined by measuring the viewing area of the microscope and multiplying the viewing area by the distance between the slide 10 and cover slip 22 as determined by the diameter of the beads 16. From the number of control particles counted within the known volume $V_y$ of water 30, a measured concentration of chicken red blood cells in the water 30 is obtained. This measured concentration of chicken red blood cells is then compared to the actual concentration of chicken red blood cells in the water.

FIGS. 4-6 also illustrate a preferred method of calibrating the viewing area of a microscope provided by the present invention. In this case, mixture 18 comprises a known concentration of chicken red blood cells in water, the chicken red blood cells being formalin-fixed so as not to lyse in the presence of a hemolysing solution. A quantity of mixture 18 is placed onto adhesive matrix 12 made of a solid residue of dried hemolysing solution. Mixture 18 and matrix 12 are mixed with a stirring instrument 20 so that matrix 12 dissolves in the water. The mixture with the adhesive matrix dissolved therein is denoted in the Figures as 30. Cover slip 22 is placed over mixture 30 and beads 16 so that cover slip 22 is spaced from slide 10 by a distance determined by the diameter of beads I6. The chicken red blood cells in mixture 30 disposed between cover slip 22 and slide 10 are viewed under magnification with a microscope to be calibrated, and the chicken red blood cells in the viewing area of the microscope are counted. A calibration factor for the viewing area of the microscope is calculated by dividing the known concentration of chicken red blood cells in mixture 18 by the number of chicken red blood cells counted in the viewing area of the microscope. An advantage of this embodiment of the invention is in providing a simple and exact method of calibration.

Figure 7:
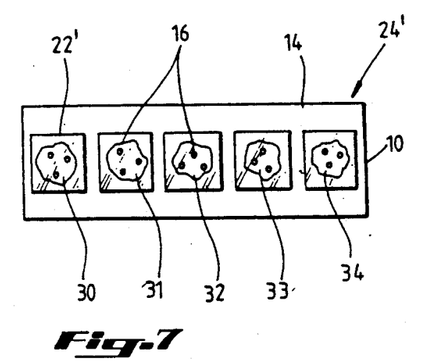
FIG. 7 is a plan view of an alternative embodiment of the counting chamber prepared in accordance with the present invention.

Referring now to FIG. 7, the present invention also provides a microscope slide 10 for use in quantifying components is a plurality of liquid samples. This microscope slide 10 is similar to the microscope slide illustrated in FIG. I, except that a plurality of spaced adhesive matrices made of dried residues of adhesive liquid are provided on the operative face 14 of the microscope slide 10. If an aqueous liquid sample to be examined, then the adhesive liquid is aqueous sucrose; if white blood cells are to be counted, the adhesive liquid is a hemolysing solution. The adhesive matrix are thus soluble in the liquid samples having components to be quantified. Each matrix contains a plurality of substantially spherical beads 16 of uniform diameter made of glass. One or more cover slips 22' for positioning over the operative face 14 of the slide 10 are provided to form a counting chamber 24'. Thus, microscope slide 10 can be used for examining several liquid samples 30, 31, 32, 33, and 34.

Figure 8:
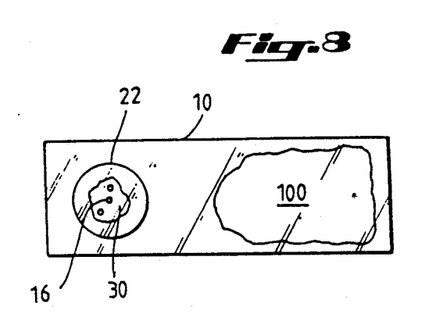
FIG. 8 is a plan view of another alternative embodiment of a counting chamber prepared in accordance with the present invention.

As shown in FIG. 8 in connection with FIG. 1, a single matrix 12 may be located proximate one end of microscope slide 10, with the other end of the microscope slide unprepared for quantification. When this is done, quantification may be performed on a portion of the slide 10, and the remaining portion may be used for some other purpose, for example, a blood smear 100 for later staining and examination.

Figure 9:
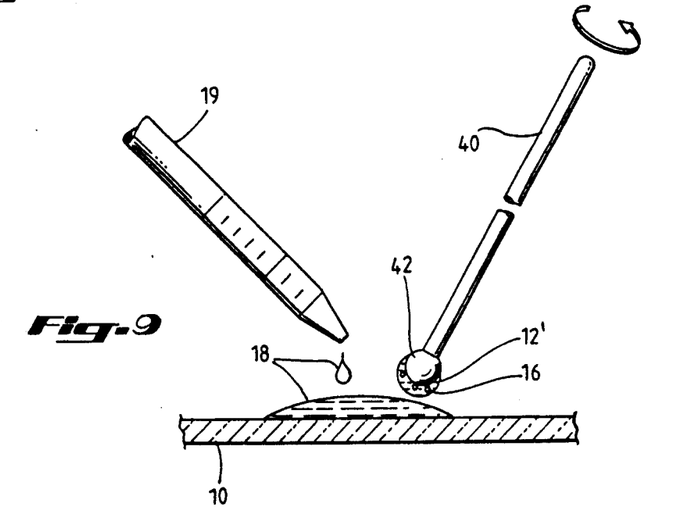
FIG. 9 is a fragmentary side view illustrating an alternative method of quantifying structural components in a liquid sample provided by the present invention.
Figure 10:
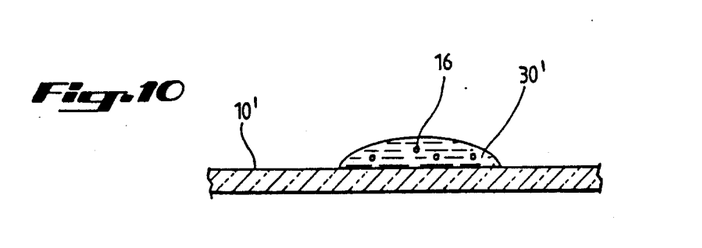
FIG. 10 is also a fragmentary, sectional side view further illustrating the method shown in FIG. 9.

FIGS. 9 and 10 illustrate an alternative method and apparatus provided by the present invention. FIG. 9 shows a stirring rod 40 for use in quantifying components in a liquid sample. Stirring rod 40 has a bulbous end portion 42 and a dried adhesive matrix 12', made of a solid residue of dried adhesive liquid over the tip of the bulbous end portion 42. (Adhesive matrix 12, is enlarged out of scale for ease of illustration). An advantage of having a bulbous end portion is that it provides a larger surface area at the tip of the stirring rod to which the adhesive matrix can adhere. If stirring rod 40 is to be used for quantification of components in an aqueous sample, the adhesive liquid consists of aqueous sucrose; if the stirring rod 40 is to be used for white blood cell counting, the adhesive liquid is a hemolysing solution. Cap 12, is thus soluble in the liquid sample to be examined. Located within the adhesive matrix 12' are substantially spherical beads 16 of uniform diameter made of glass. The adhesive matrix 12' is analogous to the adhesive matrix 12 on the microscope slide illustrated in FIG. 1.

Figure 3B:
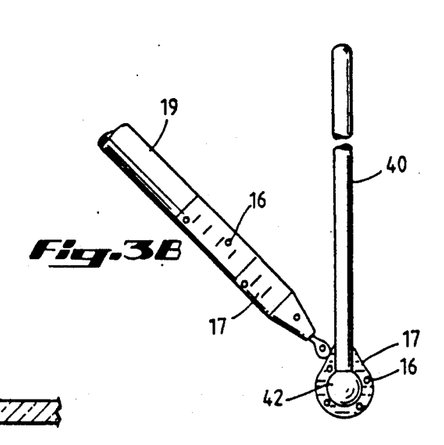
FIG. 3B is a side view illustrating a method for preparing a preferred embodiment of a stirring rod in accordance with the present invention.

FIG. 2 and 3B illustrate a preferred method for preparing stirring rod 40. A plurality of glass beads 16 are mixed in adhesive liquid 17. Stirring rod 40 is held in a vertical position so that bulbous end portion 42 is pointed downwards. A quantity of the mixture of beads 16 and adhesive liquid 17 are applied to the bulbous end portion 42 of stirring rod 40 by means of pipette 19, and the mixture is allowed to flow down to the lower tip of the stirring rod 40. Adhesive liquid 17 is allowed to dry to form the adhesive matrix 12' illustrated in FIG. 9

A method for quantifying components in a liquid sample is illustrated by FIGS. 9 and 10. Aqueous sample 18 is placed on microscope slide 10' and stirred with rod 40 so that at least a portion of adhesive matrix 12' is dissolved in the liquid sample 18, thereby mixing a plurality of beads 16 in the liquid sample 18. In FIG. 10, the liquid sample with adhesive matrix 12' dissolved therein and beads 16 dispersed therein is denoted by 30'. Components within sample 30, may now be quantified in a method analogous to that illustrated by FIGS. 5 and 6. That is, a cover slip 22 is placed over the sample, now 30', and beads 16 so that the cover slip 22 rests on the beads 16 and is spaced from the slide, now 10', by a known distance determined by the diameter of the beads 16. The sample 30' disposed between the slide 10' and cover slip 22 is then viewed under magnification with a microscope. The components in a known volume of the sample 30' are counted. The volume is determined by measuring the viewing area of the microscope and multiplying the viewing area by the distance between the slide 10' and cover slip 22 as determined by the diameter of the beads 16.

A method for counting white blood cells is also provided by the present invention when the matrix 12' of stirring rod 40 illustrated in FIG. 9 comprises a solid residue of dried hemolysing solution. In this case, blood sample 18 is placed on microscope slide 10' and stirred with stirring rod 40 until at least a portion of the matrix 12' is dissolved within blood sample 18, so that a plurality of beads 16 are mixed in the blood, and the red blood cells in the blood are lysed by the hemolysing constituents from the matrix 12'. In FIG. 10, 30' now represents the blood sample with the red blood cells lysed, so that the white blood cells can be counted, in accordance with the method described above.

The following examples are designed to illustrate certain aspects of the present invention. However, they should not be construed as limiting the claims thereof.

EXAMPLE I

A typical laboratory experiment comparing the present method of white blood cell counting with counts using a Coulter Counter yielded the results in Table I below. White blood cell counts on five samples of the same blood specimen were conducted on a microscope slide using beads having nominal diameter of 36 microns. Blood samples having volume of 5 microliters were used. The blood was five days old and had been kept at room temperature for three days. For each of the five samples, four microscopic fields were examined. This was accomplished by counting the cells in one field, randomly moving the slide to view and count cells in another field, and repeating this procedure until four fields were viewed for each sample.

TABLE I

| Microscopic Field Counted | Sample # | | | | |
|---|---|---|---|---|---|
| | 1 | 2 | 3 | 4 | 5 |
| A | 71* | 75 | 73 | 67 | 60 |
| B | 66 | 79 | 77 | 58 | 60 |
| C | 82 | 64 | 70 | 71 | 83 |
| D | 81 | 61 | 64 | 59 | 59 |
| $\bar{x}$ | 75 | 70 | 71 | 64 | 66 |
| $\sigma$ | 7.8 | 8.6 | 5.4 | 6.3 | 11.7 |

*(wbc counted/field)

where $\bar{x}$ is the number of cells counted for each sample averaged over the four microscopic fields, and $\sigma$ is the standard deviation for each sample over the four fields. Overall $\bar{x}$ and overall $\sigma$ reflect the averages of the five samples.

Taking the average of the five $\bar{x}$ values, an overall $\bar{x}$ was calculated as 69.2. The overall $\sigma$ for the five $\bar{x}$ values was 4.3.

From these results, the white blood cell (wbc) count was calculated:

$$wbc/mm^3 = \frac{\text{average count in field}}{\text{volume of blood in field}}$$

$$= \frac{\text{average count in field}}{(\text{area of field}) \times (\text{diameter of beads})}$$

$$= \frac{69.2 \ wbc}{0.00694 \ mm^3}$$

$$= 9,971 \ wbc/mm^3$$

In comparison, the white blood cell count obtained from a Coulter Counter for the same blood specimen was 9,800 wbc/mm$^3$.

A coefficient of variation (c.v.) can be calculated by the following:

$$c.v. = \frac{\text{overall } \sigma}{\text{overall } \bar{x}} \times 100\%$$

$$= \frac{4.3}{69.2} \times 100\% = 6.2\%$$

This should be compared with the theoretical coefficient of variation (t.c.v.):

$$l.c.v. = \frac{\sqrt{n}}{n} \times 100\%$$

$$= \frac{\sqrt{277}}{277} \times 100\% = 6.0\%$$

where n is the average of the total cells counted in the four fields for each sample.

EXAMPLE II

To show a correlation between the method of the present invention (the "bead method") and a Coulter Counter method, a series of white blood cell (wbc) counts was performed on 15 different blood specimens. Beads having nominal diameter of 50 microns were used and the cells were counted under a microscope with a reticle having nominal viewing area dimensions of 0.45 mm×0.45 mm. Three to five counts were performed on each specimen to yield an average ($\bar{x}$) for each specimen as shown in Table II.

TABLE II

| | Bead Method Specimen # | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Cells | 153 | 114 | 123 | 134 | 115 | 74 | 66 | 149 | 73 | 75 | 138 | 89 | 81 | 113 | 47 |
| counted | 134 | 117 | 104 | 153 | 126 | 64 | 58 | 139 | 61 | 75 | 166 | 97 | 78 | 113 | 53 |
| in field | 150 | 77 | 113 | 140 | 100 | 80 | 45 | 134 | 61 | 64 | 136 | 90 | 81 | 100 | 58 |
| | 91 | 103 | | | 79 | 58 | | 63 | 79 | 179 | | 77 | | 52 | |
| | | 75 | | | | | | | | 161 | | | | | |
| $\bar{x}$ | 146 | 95 | 111 | 142 | 114 | 74 | 57 | 141 | 66 | 73 | 159 | 92 | 79 | 109 | 52.5 |

The cells in each specimen were also counted by a Coulter Counter, as shown in Table III. A calibration factor (c.f.) was calculated for the viewing area of the reticle by dividing the count from the Coulter Counter for each specimen by the average cells counted in the field by the bead method. The bead method count (in wbc/mm$^3$) was thus calculated by multiplying the average cells counted in the field ($\bar{x}$) by the average calibration factor (c.f.). The results are shown in Table III.

TABLE III

| Sample # | Bead Method: Cells in field | Coulter Counter: (wbc/mm$^3$) × 10$^{-3}$ | c.f. (mm$^{-3}$) | Bead Method: (wbc/mm$^3$) × 10$^{-3}$ |
|---|---|---|---|---|
| 1 | 146 | 15.0 | 103 | 14.5 |
| 2 | 95 | 8.9 | 94 | 9.4 |
| 3 | 111 | 9.5 | 86 | 11.0 |
| 4 | 142 | 15.1 | 106 | 14.1 |
| 5 | 114 | 11.6 | 102 | 11.3 |
| 6 | 74 | 7.0 | 95 | 7.3 |
| 7 | 57 | 5.5 | 96 | 5.6 |
| 8 | 141 | 13.8 | 98 | 14.0 |
| 9 | 66 | 6.4 | 97 | 6.5 |
| 10 | 73 | 6.6 | 90 | 7.2 |
| 11 | 159 | 17.1 | 108 | 15.7 |
| 12 | 92 | 9.4 | 102 | 9.1 |
| 13 | 79 | 8.6 | 109 | 7.8 |
| 14 | 109 | 10.6 | 97 | 10.8 |
| 15 | 53 | 5.4 | 102 | 5.3 |
| | | | $\overline{c.f.}$ = 99 | |

By comparing the counts obtained by the two methods, a statistical coefficient of correlation was calculated as 0.985, showing that the two methods yield substantially similar results.

The instant invention has been disclosed in connection with specific embodiments. However, it will be apparent to those skilled in the art that variations from the illustrated embodiments may be undertaken without departing the spirit and scope of the invention.

What is claimed is:

1. A method for quantifying components in a liquid sample, comprising:
    placing a liquid sample on a dried adhesive matrix ona microscope slide, said matrix being soluble in the liquid sample and having located therein a plurality of substantially spherical beads of uniform diameter made of a substantially non-compressible material;
    mixing the liquid sample and matrix with a stirring instrument so tht thematrix dissolves inthe liqiud sample;
    plcing a cover slip over the sample and beads so that the cover slip rests on the beads and is spaced from the slide by a known distance determined by the diameter of the beads;
    viewing the sample disposed between the slide and cover slip under magnification with a microscope; and
    counting the components in a known volume of the sample, wherein the volume is determined by measuring the viewing area of the microscope and multiplying the viewing area by the distance between the slideand cover slip as determined by the diameter of the beads.

2. The method of claim 1, wherein the number of beads between the slide and cover slip is between about 5-30 per square centimeter.

3. The method of claim 1, wherein the beads are made of glass.

4. The method of claim 1, wherein the diameter of each bead is between about 2-200 microns.

5. A method for counting white blood cells, comprising:
    placing a sample of blood on a dried adhesive matrix ona microscope slide, sidmatrix having located therein a pluralityof substantially spherical beads of uniform diameter made of a substantially non-compressible material, and said matrix comprising a solid residue of dried hemolysing solution soluble in the blood sample and capable of selectively lysing red blood cells;

mixing the blood sample and matrix with a stirring instrument so that the matrix dissolves in the blood sample and the red blood cells in the blood sample are lysed by hemolysing constituents from the matrix;

placing a cover slip over the blood sample and beads so that the cover slip rests on the beads and is spaced from the slide by a known distance determined by the diameter of the beads;

viewing the blood sample disposed between the slide and cover slip under magnification with a microscope; and counting the white blood cells in a known volume of the blood sample, wherein the volume is determined by measuring the viewing area of the microscope and multiplying the viewing area by the distance between the slide and cover slip as determined by the diameter of the beads.

6. The method of claim 5, wherein the beads are made of glass.

7. The method of claim 5, wherein the diameter of each bead is between about 2–200 microns.

8. The method of claim 5, wherein the number of beads between the slide and cover slip is between about 5–30 per square centimeter.

9. A method for quantifying components in a liquid sample, comprising:

placing a liquid sample on a microscope slide;

stirring the liquid sample with a stirring rod having a dried adhesive matrix over at least one end thereof, said matrix being soluble in the liquid sample and having located threin a plurality of substantially spherical beads of uniform diameter made of a substantially non-compressible material, so that at least a portion of the matrix is dissolved in the liquid sample, thereby mixing a plurality of beads in the liquid sample;

placing a cover slip over the sample and beads so that the cover slip rests on the beads and is spaced from the slide by a known distance determined by the diameter of the beads;

viewing the sample disposed between the slide and cover slip under magnification with a microscope; and counting the components in a known volume of the sample, wherein the volume is determined by measuring the viewing area of the microscope and multiplying the viewing area by the distance between the slide and cover slip as determined by the diameter of the beads.

10. The method of claim 9, wherein the beads re made of glass.

11. The method of claim 9, wherein the diameter of each bead is between about 2–200 microns.

12. The method of claim 9, wherein the number of beads between the slide and cover slip is between about 5–30 per square centimeter.

13. A method for counting white blood cells, comprising:

placing a sample of blood on a microscope slide;

stirring the blood sample with a stirring rod havinga dried adhesive matrix over at least one end therof, said matrix having a located therein a plurality of substantially spherical beads of uniform diameter made of a substantially non-compressible material, and said matrix comprising a solid residue of dried hemolysing solution soluble in the blood sample and capable of seletively lysing red blood cells, until at least aportoin of the mtrix is dissolved in the blood sample, so that a pluraty of beads are mixed in the blood sample, and the red blood cells in the blood sample are lysed by hemolysed constituents from the matrix;

placing a cover slip over the blood sample and beads so that the cover slip rests on the beads and is spaced from the slide by a known distance determined by the diameter of the beads;

viewing the blood sample disposed between the slide and cover slipunder magnification with a microscope; and counting the white blood cells in a known volume of the blood sample, wherein the volume is determined by measuring the viewing area of the microscope and multiplying the viewing area by the distance between the slide and cover slip as determined by the diameter of the beads.

14. The method of claim 13, wherein the beads are made of glass.

15. The method of claim 13 wherein the diameter of each bead is between about 2–200 microns.

16. The method of claim 13 wherein the number of beads between the slide and cover slip is between about 5–30 per square centimeter.

17. A method for testing the reliability of a white blood cell counting method, comprising:

placing a known volume Vx of water on a dried adhesive matrix on amicroscope slide, said matrix comprising a solid residue of dried hemolysing solution soluble inwter and capable of selectively lysing red blood cells, and said matrix having located therein a plurality of substantially spherical beads of uniform diameter made of substantially non-compressible material, and also having located therein a known number of control particles, fixed so as not to be destroyed by drying or lyse in the presence of the hemolysing solution, and shaped and sized so as to simulate human white blood cells;

mixing the water and matrix with a stirring instrument so that the matrix dissolves in the water;

calculatring the actual concentration of control particles in the water based on the known number of particles in the matrix and volume Vx of water;

placing a cover slip over the water and beads so that the cover slip rests on the beads and is spaced from the slide by a known distance determined by the diameter of the beads;

viewing the control particles in the water disposed between the slide and cover slip under magnification with a microscope;

counting the control particles in a known volume Vy of water, wherein the volume Vy is determined by measuring the viewing area of the microscope and multiplying the viewing area by the distance between the slide and cover slip as determined by the diameter of the beads, to obtain a measured concentration of control particles in the water; and comparing the measured concentration of control particles in the water with the actual concentration of control particles in the water.

18. The method of claim 17, wherein the volume Vx of water is selected so that the actual concentration of control particles in the water after dissolving the matrix in the water will be between about 5,000–10,000 particles/cubic millimeter.

19. A method for calibrating the viewing area of a microscope, comprising:

mixing a plurality of control particles in water, the concentration of the control particles in the water being exact and known;

placing a quantity of the mixture of control particles and water on a dried adhesive matrix on a microscope slide, sidmatrix being soluble in water and hvaing located therein a plurality of substantially spherical beads of uniform diameter made of a substantially non-compressible material;

mixing the water and matrix with a stirring instrument so that the matrix dissolves in the water;

placing a cover slip over the mixture and beads os that the cover slip rests on the beads and is spaced from the slide by a distance determined by the diameter of the beads;

viewing the control particles in the water disposed between the slide and cover slip under magnification with a microscope to be calibrated;

counting the control particles in the viewing area of the microscope; and calculating a calibration factor for the viewing area of the microscope, by dividing the known concentration of control particles in water by the number of control particles counted in the viewing area of the microscope.

20. The method of claim 19, wherein the adhesive matrix comprises a solid residue of dried hemolysing solution capable of selectively lysing red blood cells, and wherein the control particles are fixed so as not to lyse in the presence of the hemolysing solution.

* * * * *

UNITED STATES PATENT AND TRADEMARK OFFICE
CERTIFICATE OF CORRECTION

PATENT NO. : 5,039,487

DATED : August 13, 1991

INVENTOR(S) : Kendall O. Smith

It is certified that error appears in the above-identified patent and that said Letters Patent is hereby corrected as shown below:

In claim 1, column 16, line 6, change "ona" to --on a--.

In claim 1, column 16, line 12, change "tht" to --that--, "thematrix" to --the matrix--, "inthe" to --in the--, and "liqiud" to --liquid--.

In claim 1, column 16, line 14, change "plcing" to --placing--.

In claim 1, column 16, line 36, change "slideand" to --slide and--.

In claim 5, column 16, line 67, change "ona" to --on a--, and "sidmatrix" to --said matrix--.

In claim 5, column 16, line 68, change "pluraltyof" to --plurality of--.

In claim 9, column 17, line 37, change "threin" to --therein--.

In claim 10, column 17, line 56, change "re" to --are--.

In claim 13, column 17, line 66, change "havinga" to --having a--.

In claim 13, column 17, line 68, delete "a" after "having".

UNITED STATES PATENT AND TRADEMARK OFFICE
CERTIFICATE OF CORRECTION

PATENT NO. : 5,039,487

DATED : August 13, 1991

INVENTOR(S) : Kendall O. Smith

It is certified that error appears in the above-identified patent and that said Letters Patent is hereby corrected as shown below:

Column 18, claim 13, line 5, change "seletively" to --selectively--.

Signed and Sealed this

Twenty-third Day of March, 1993

*Attest:*

STEPHEN G. KUNIN

*Attesting Officer*      *Acting Commissioner of Patents and Trademarks*